US010575989B2

(12) United States Patent
Dishler et al.

(10) Patent No.: US 10,575,989 B2
(45) Date of Patent: Mar. 3, 2020

(54) EYE SURGICAL PROCEDURE

(71) Applicant: Carl Zeiss Meditec AG, Jena (DE)

(72) Inventors: Jon Dishler, Greenwood Village, CO (US); Mark Bischoff, Jena (DE)

(73) Assignee: CARL ZEISS MEDITEC AG, Jena (DE)

( * ) Notice: Subject to any disclaimer, the term of this patent is extended or adjusted under 35 U.S.C. 154(b) by 167 days.

(21) Appl. No.: 15/281,097

(22) Filed: Sep. 30, 2016

(65) Prior Publication Data

US 2017/0087021 A1    Mar. 30, 2017

Related U.S. Application Data

(60) Provisional application No. 62/234,697, filed on Sep. 30, 2015.

(51) Int. Cl.
    *A61F 9/008*    (2006.01)
(52) U.S. Cl.
    CPC ........ *A61F 9/00827* (2013.01); *A61F 9/0084* (2013.01); *A61F 2009/00872* (2013.01); *A61F 2009/00878* (2013.01)
(58) Field of Classification Search
    CPC .. A61F 2009/00872; A61F 2009/00878; A61F 9/0084; A61F 2009/00827; A61F 9/00827
    See application file for complete search history.

(56) References Cited

U.S. PATENT DOCUMENTS

| 5,656,186 | A | 8/1997 | Mourou et al. |
| 6,110,166 | A * | 8/2000 | Juhasz ............... A61F 9/008 128/898 |
| 2007/0244472 | A1 | 10/2007 | Kuhn et al. |
| 2008/0183159 | A1 | 7/2008 | Preuss et al. |
| 2011/0224657 | A1* | 9/2011 | Stevens ............... A61F 9/008 606/5 |
| 2014/0128855 | A1* | 5/2014 | Wottke ............... A61F 9/00827 606/5 |
| 2015/0150722 | A1 | 6/2015 | Russmann et al. |
| 2015/0374548 | A1 | 12/2015 | Wottke et al. |

FOREIGN PATENT DOCUMENTS

| DE | 69500997 T2 | 4/1998 |
| DE | 102005040338 A1 | 3/2007 |
| DE | 102007019813 A1 | 10/2008 |
| DE | 102013004688 A1 | 9/2014 |

* cited by examiner

*Primary Examiner* — Lynsey C Eiseman
*Assistant Examiner* — Amanda L Steinberg
(74) *Attorney, Agent, or Firm* — Leydig, Voit & Mayer, Ltd.

(57) ABSTRACT

A planning system for generating control data for a treatment device for eye surgery that creates at least two incision surfaces in the cornea using a laser apparatus is provided. The planning system includes a processor configured to specify the cornea incision surfaces based on data of a refractive correction, the cornea incision surfaces including an lenticule incision and a cap incision, at least one of the cap incision or the lenticule incision being irregularly shaped and having extensions to the surrounding tissue, and generate a control data record for the cornea incision surfaces for purposes of controlling the laser apparatus.

18 Claims, 4 Drawing Sheets

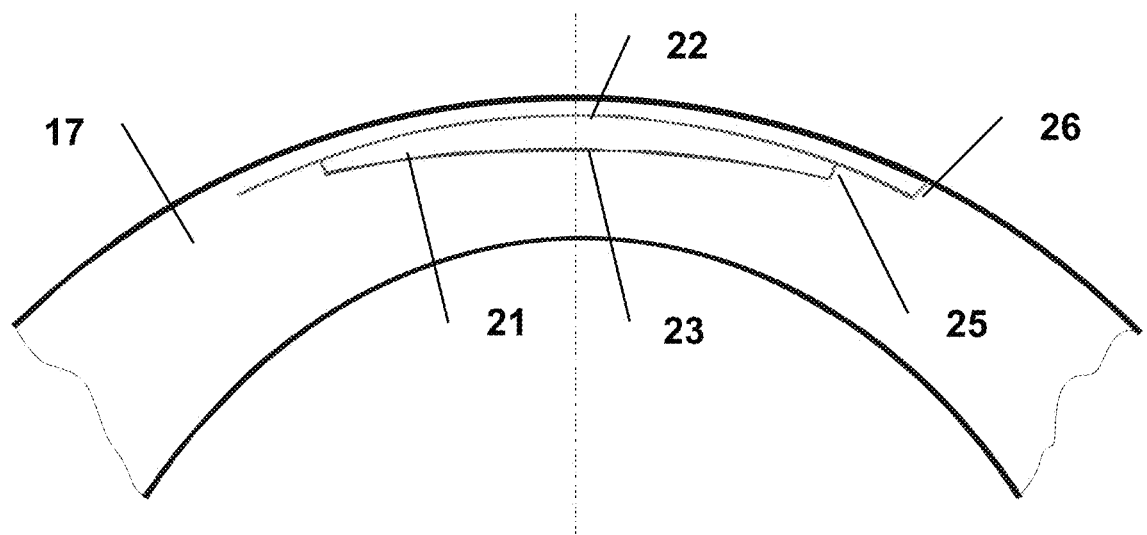
Fig. 6 (a) (Prior Art)
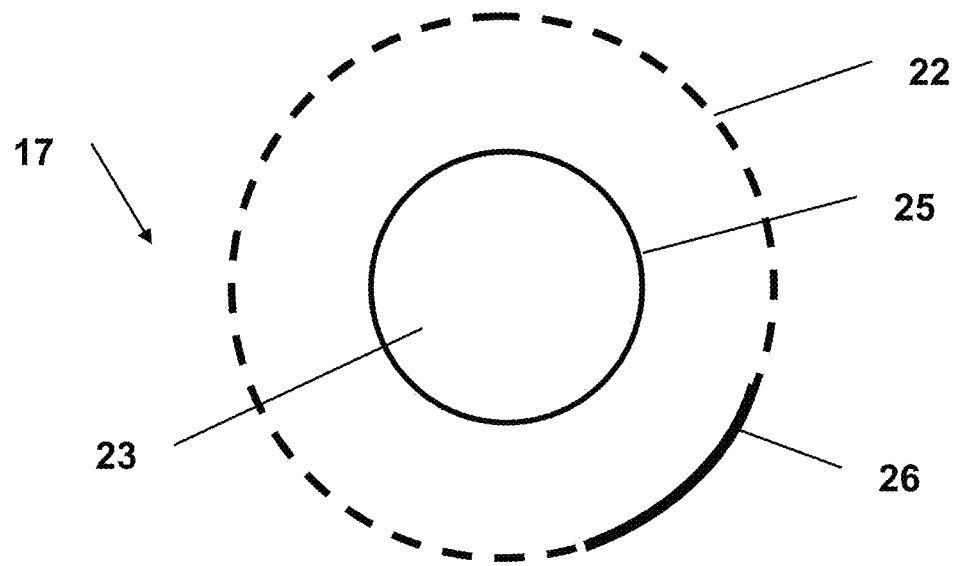
Fig. 6 (b) (Prior Art)

EYE SURGICAL PROCEDURE

CROSS REFERENCE TO RELATED APPLICATIONS

This application claims benefit to U.S. Provisional Patent Application No. 62/234,697, filed Sep. 30, 2015.

FIELD

The invention relates to a planning system for generating control data for a laser apparatus treatment device, to a laser apparatus treatment device having such a planning system, and to a method for generating control data for a laser apparatus treatment device. The invention also relates to a method for eye surgery using a laser apparatus treatment device.

BACKGROUND

The state of the art comprises a wide variety of treatment methods with the objective of performing refractive correction of the human eye. The objective of the operation methods is to systematically reshape the cornea in order to influence the light refraction in the eye. Various operation methods are used for this purpose. The most widespread implementation is the so-called Laser-Assisted In Situ Keratomileusis, also abbreviated LASIK. In this procedure a flap is cut from the surface of the cornea on one side and folded back. This flap can be cut by means of a mechanical microkeratome or else by means of a so-called femtosecond laser keratome of the type sold, for example, by Intralase Corp. of Irvine, Calif., United States. Once the flap has been cut and folded back, the LASIK surgery provides for the use of an excimer laser that ablates the cornea tissue underneath the flap that has been exposed in this manner. After the volume located underneath the surface of the cornea has been vaporized in this manner, the cornea flap is folded back into its original position.

The use of a laser keratome to expose the flap is advantageous in comparison to employing a mechanical blade since the geometrical precision is improved and the frequency of clinically relevant complications is diminished. In particular, the flap can be created with a much more constant thickness by using laser radiation. Moreover, the edge of the incision is precisely shaped, reducing the risk of healing problems due to this boundary surface that is left over after the operation. However, a drawback of this method is that two different treatment devices have to be used, namely, the laser keratome that exposes the flap and the laser that vaporizes the cornea tissue.

These drawbacks are overcome with a method that was recently implemented by Carl Zeiss Meditec AG and that is abbreviated as FLEx (Femtosecond Lenticule Extraction). This method for lenticule extraction employs a short-pulse laser, preferably a femtosecond laser, to create an incision geometry in the cornea, separating a cornea volume (so-called lenticule) in the cornea. This volume is then removed manually by the surgeon after the flap covering the lenticule has been folded back. The advantage of this method is, for one thing, that the quality of the incision is further improved by using a femtosecond laser combined with a curved contact glass. Secondly, only a single treatment device is needed; the excimer laser is no longer used. This method also avoids risks and limitations of the excimer laser.

A refinement of the FLEx method is referred to in the literature today as the SMILE (Small Incision Lenticule Extraction) method in which no flap is created but rather only a small opening incision that serves to access the lenticule located beneath the so-called cap. The separated lenticule is removed through this small opening incision, as a result of which the biomechanical integrity of the anterior cornea is less affected than in the LASIK, or similar methods. Moreover, in this manner, fewer superficial nerve fibers in the cornea are cut and this is likely to be advantageous when it comes to the restoration of the original sensitivity of the surface of the cornea. As a result, the symptom of dry eyes that often has to be treated after a LASIK procedure is often less severe and less protracted. Other complications after LASIK, which usually have to do with the flap (e.g. displaced flap, folds, epithelial ingrowth in the flap bed) occur less often in procedures without a flap.

When incision surfaces are made in the cornea by means of laser radiation, the optical radiation effect is normally utilized in that a photodisruption is created by means of individual optical pulses whose duration can be between about 100 fs and 100 ns. It is also a known procedure to apply individual pulses whose energy lies below a threshold value for a photodisruption into the tissue or material with such an overlap that this also achieves a material or tissue separation. This concept for creating an incision in the cornea tissue allows a wide variety of incisions. For clinical reasons, it can be advantageous for the diameter of the cap incision, which defines the anterior surface of the lenticule to be selected larger than that of the lenticule incision, which defines the diameter and posterior surface of the lenticule. See, for example, US Patent Application Publication No. 2014/0128855.

SUMMARY

In an embodiment, the present invention provides a planning system for generating control data for a treatment device for eye surgery that creates at least two incision surfaces in the cornea using a laser apparatus. The planning system includes a processor configured to specify the cornea incision surfaces based on data of a refractive correction, the cornea incision surfaces including an lenticule incision and a cap incision, at least one of the cap incision or the lenticule incision being irregularly shaped and having extensions to the surrounding tissue, and generate a control data record for the cornea incision surfaces for purposes of controlling the laser apparatus.

BRIEF DESCRIPTION OF THE DRAWINGS

The present invention will be described in even greater detail below based on the exemplary figures. The invention is not limited to the exemplary embodiments. All features described and/or illustrated herein can be used alone or combined in different combinations in embodiments of the invention. The features and advantages of various embodiments of the present invention will become apparent by reading the following detailed description with reference to the attached drawings which illustrate the following:

FIGS. 6 A and B show a schematic view of a SMILE lenticule geometry according to the state of the art.

DETAILED DESCRIPTION

Figure 1:
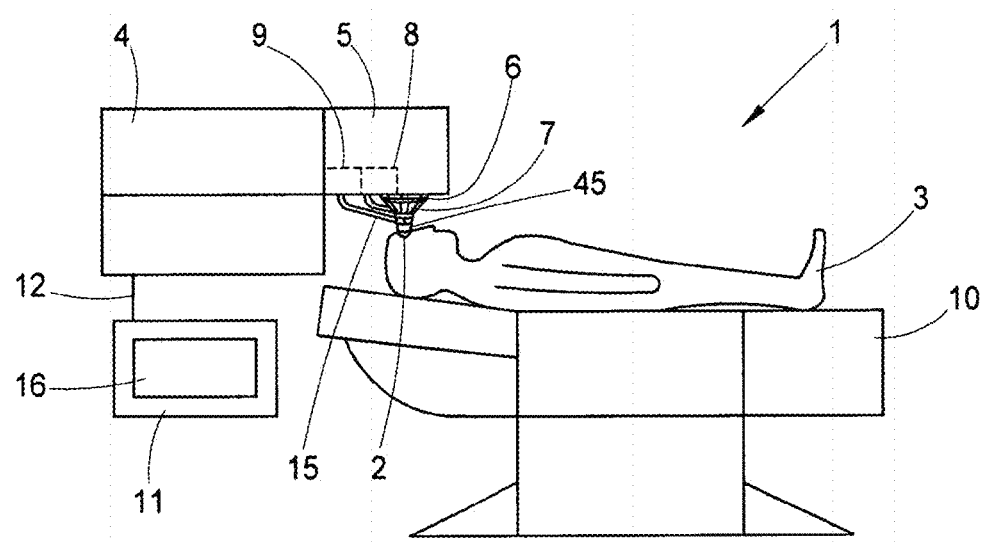
FIG. 1 shows a schematic representation of a treatment device with a planning system for a treatment to carry out a refractive correction by means of eye surgery according to an embodiment of the invention.

A planning system for generating control data for a treatment device for eye surgery is described herein that creates at least two incision surfaces in the cornea using a laser apparatus. The planning system includes a computation device configured to specify the cornea incision surfaces based on data of a refractive correction. The cornea incision surfaces include a cap incision and a lenticule incision, with either or both of these incisions being irregularly shaped and having extensions to the surrounding tissue. The computation device being configured to generate a control data record for the cornea incision surfaces for purposes of controlling the laser apparatus. For the purpose of clarity irregularly shaped does mean that the cap and/or lenticule incision(s) is not circular or elliptical when seen along the visual axis of the eye but has a number of extension where the extensions can be placed symmetrically at the circumference of the cap incision or also asymmetrically.

Such an irregularly shaped cap incision can result in higher quality incisions and therefore better surgical outcomes. Creation of these unique incision surfaces is not an obvious benefit, but in practice provides improved tissue separation. The mechanism by which improved tissue separation is achieved appears to be improved pressure equalization.

Embodiments of the present invention provide a planning system for generating control data, a treatment device for refraction-correcting eye surgery, and a method for generating control data for such a treatment device, which ensures an improved form of cap incision.

Embodiments of the invention provide a planning system having a processor configured to specify a cornea incision surface, whereby the processor specifies the cap incision in such a way that it is irregularly shaped and has extensions to the surrounding tissue.

In an embodiment, the invention provides a treatment device having a laser apparatus that cuts at least one incision surface in the cornea using laser radiation on the basis of control data, and having a planning system for generating the control data, whereby the planning system specifies the cap incision in such a way it is irregularly shaped and has extensions to the surrounding tissue.

In an embodiment, the invention provides a method for generating control data, the method that includes generating a control data record for the cornea incision surface for purposes of controlling the laser apparatus, wherein a planning system specifies the cap incision in such a way that it is irregularly shaped and has extensions to the surrounding tissue.

In an embodiment, the invention provides a method that includes generating a control data record for the cornea incision surface, transmitting the control data to the treatment device, and creating the incision surfaces by controlling the laser apparatus on the basis of the control data record, whereby, when the control data record is generated, the cap incision surface is specified in such a way it is irregularly shaped and has extensions to the surrounding tissue.

The cap incision, i.e. the incision that runs largely parallel to the surface of the cornea, is selected to be larger than the diameter of the lenticule. Moreover, according to the invention, an opening incision or access incision is created whose position is between the outer edges of the cap incision and the edge of the lenticule incision. This access incision can preferably be shaped like a circular segment or a strip. This opening incision can be placed in a portion of the cap incision remote from the irregular area or at a specific location in the irregular area.

In another embodiment the most off-center point of the cap incision is selected to have an outer radius that is greater than the radial distance of the radial opening cut. In another embodiment the most off-center point of the lenticule incision, i.e. the posterior incision that separates the lenticule from the underlying stroma, is selected to have an outer radius that is greater than the radial distance of the internal side cut, which circumferentially connects lenticule incision and cap incision. Another embodiment has both the lenticule and cap incisions have extensions beyond either the internal sidecut and opening incision. There are four incision planes—cap cut, lenticule cut, internal sidecut (defines lenticule diameter), and opening incision.

A treatment device for eye surgery is shown in FIG. 1 and designated by the general reference numeral 1. The treatment device 1 is configured to create laser incisions in the eye 2 of a patient 3. For this purpose, the treatment device 1 has a laser apparatus 4 that emits a laser beam 6 from a laser source 5 and that focuses this laser beam 6 as a focused beam 7 into the eye 2 or the cornea. Preferably, the laser beam 6 is a pulsed laser with a wavelength between 300 nanometers and 10 micrometers. Moreover, the pulse length of the laser beam 6 is in the range between 1 femtosecond and 100 nanoseconds, whereby pulse repetition rates of 50 kHz to 5000 kHz and pulse energies between 0.01 microjoule and 0.01 millijoule are possible. The treatment device 1 thus makes an incision surface in the cornea of the eye 2 by deflecting the pulsed laser radiation. For this reason, a scanner 8 as well as a radiation intensity modulator 9 are also provided in the laser apparatus 4 or in its laser source 5.

The patient 3 lies on a table 10 that can be adjusted in three spatial directions in order to suitably orient the eye 2 with respect to the incident laser beam 6. In a preferred set-up, the table 10 can be adjusted by a motor.

The regulation can especially be carried out by a control unit 11 that fundamentally controls the operation of the treatment device 1 and, for this purpose, is in communication with the treatment device via suitable data connections, for example, connection lines 12. Of course, this communication can also be achieved by other modalities, for example, via optical conductors or wirelessly. The control unit 11 performs the appropriate settings, the time control of the treatment device 1, especially of the laser apparatus 4, and thus effectuates corresponding functions of the treatment device 1.

The treatment device 1 also has a fixation device 15 that fixes the position of the cornea of the eye 2 relative to the laser apparatus 4. This fixation device 15 can comprise a known contact glass 45 against which the cornea of the eye is secured by negative pressure and that gives the cornea the desired geometric shape. Such contact glasses are known to the person skilled in the art, for example, from German patent application DE 10 2005 040338 A1. The disclosed content of this publication is encompassed in its entirety here, insofar as the description comprises a model of the possible contact glass 45 for the treatment device 1.

Other modified or improved contact glass designs would also provide benefit in this inventions and are included in the scope of this patent application.

The treatment device 1 also has a camera (not shown here) that can take a picture of the cornea 17 through the contact glass 45. In this context, the illumination for the camera can be in the visible as well as in the infrared light spectrum.

The control unit 11 of the treatment device 1 also has a planning system 16 that will be explained in greater detail below.

Figure 2:
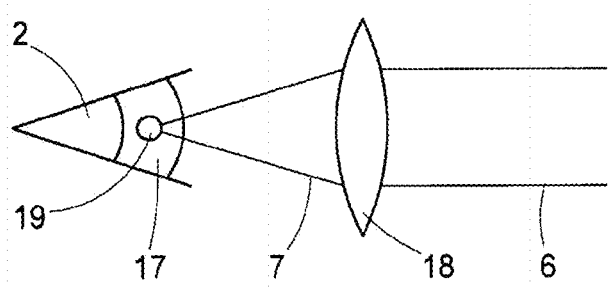
FIG. 2 shows a schematic representation of the effect of the laser radiation that is used in the treatment device of FIG. 1.

FIG. 2 schematically shows the mode of operation of the incident laser beam 6. The laser beam 6 is focused and, as the focused laser beam 7, it strikes the cornea 17 of the eye 2. A schematically drawn lens 18 is provided for purposes of focusing. In the cornea 17, this lens brings about a focus in which the laser radiation energy density is so high that, in combination with the pulse length of the pulsed laser radiation 6, a non-linear effect occurs in the cornea 17. For example, each pulse of the pulsed laser radiation 6 in the focus 19 can generate a photodisruption in the cornea 17 which, in turn, initiates a plasma bubble only schematically shown in FIG. 2. When the plasma bubble is formed, the tissue layer separation comprises a larger region than the focus 19, even though the conditions for generating the photodisruption are only achieved in the focus 19. In order for a photodisruption to be generated by each laser pulse, the energy density, i.e. the fluence of the laser radiation, has to be above a certain, pulse-length-dependent threshold value. The person skilled in the art is familiar with this situation, for example, from DE 69500997 T2, a translation from a European patent. As an alternative, a tissue separating effect can also be attained by pulsed laser radiation in that several laser radiation pulses are emitted in a given range, whereby the focal spots overlap. Then several laser radiation pulses work together to achieve a tissue-separating effect. The type of tissue separation that the treatment device 1 uses, however, is not relevant for the description below; all that is relevant is that an incision is made in the cornea 17 of the eye 2.

This invention improves the pressure equalization over the area of the plasma bubbles while they are being created thus improving cutting quality by reducing the tissue distortion during the cutting process.

In order to perform refractive correction by means of eye surgery, the laser radiation 6 removes a cornea volume from a region inside the cornea 17 in that tissue layers that isolate the cornea volume are separated there and then permit the cornea volume to be removed. In order to isolate the cornea volume that is to be removed, for instance, when applying pulsed laser radiation, the position of the focus 17 of the focused laser radiation 7 in the cornea 17 is adjusted. This is shown schematically in FIG. 3. The refractive properties of the cornea 17 are systematically changed by the removal of the volume so as to attain the envisaged refractive correction. The volume is thus usually lenticular and is referred to as a lenticule.

Figure 3:
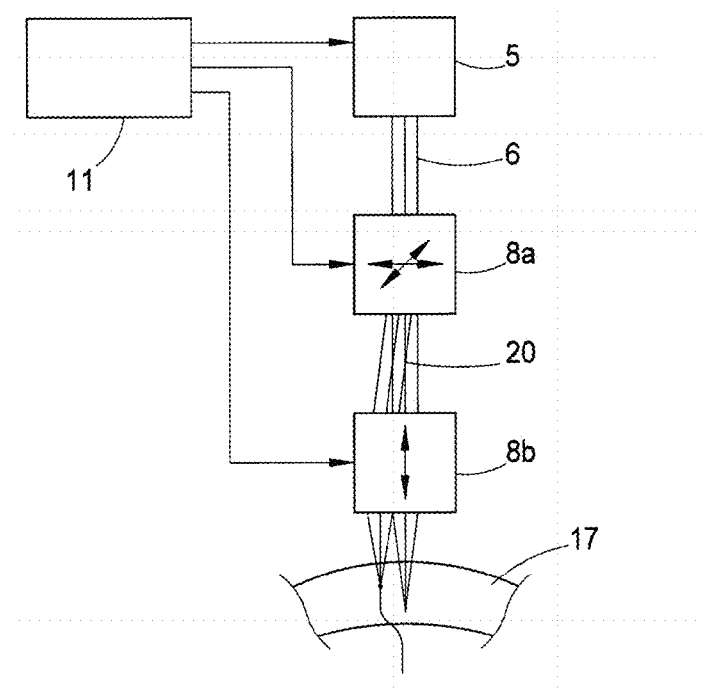
FIG. 3 shows another schematic representation of the treatment device shown in FIG. 1 for the application of the laser radiation.

FIG. 3 shows the elements of the treatment device 1 only to the extent that they are needed for purposes of elucidating the creation of the incision surface. The laser beam 6, as already mentioned, is bundled in a focus 19 in the cornea 17, and the position of the focus 19 in the cornea is adjusted to that, in order to make the incision surface, focusing energy from laser radiation pulses is applied to the tissue of the cornea 17 in various places. The laser radiation 6 is preferably provided in the form of pulsed radiation by the laser source 5. The scanner 8 is structured in two parts in the set-up shown in FIG. 3 and it consists of an xy-scanner 8a that, in one variant, is implemented by two essentially orthogonally deflecting galvanometer mirrors. The scanner 8a two-dimensionally deflects the laser beam 6 stemming from the laser source 5, so that a deflected laser beam 20 is present downstream from the scanner 9. The scanner 8a thus brings about an adjustment of the position of the focus 19 essentially perpendicular to the main direction of incidence of the laser beam 6 in the cornea 17. In order to adjust the depth position, the scanner 8 has, aside from the xy-scanner 8a, also a z-scanner 8b that is configured, for example, as an adjustable telescope is changed. The z-scanner 8b ensures that the z-position of the focus 19 is changed, i.e. its position on the optical axis of incidence. The z-scanner 8b can be installed upstream or downstream from the xy-scanner 8a.

The association of the individual coordinates with the spatial directions is not essential for the operating principle of the treatment device 1 nor, by the same token, is the fact that the scanner 8a deflects around axes that are at a right angle to each other. Rather, any scanner can be used that is capable of adjusting the focus 19 in a plane that does not encompass the axis of incidence of the optical radiation. Moreover, any desired non-Cartesian coordinate system can be employed for purposes of deflecting or regulating the position of the focus 19. Examples of this are spherical coordinates or cylindrical coordinates. The position of the focus 19 is controlled by the scanners 8a, 8b under actuation by the control unit 11 that establishes the appropriate settings of the laser source 5, of the modulator 9 (not shown in FIG. 3), and of the scanner 8. The control unit 11 ensures proper operation of the laser source 5 as well as the three-dimensionally focus adjustment described here by way of example, so that ultimately, an incision surface is created that isolates a specific cornea volume that is to be removed for purposes of refractive correction.

The control unit 11 functions in accordance with control data that is prescribed as target points for the focus adjustment, for example, in the case of the laser apparatus 4 described here merely by way of an example. As a rule, the control data is compiled in a control data record. This results in geometric specifications as a pattern for the incision surface that is to be created, for example, the coordinates of the target points. In this embodiment, the control data record then also contains concrete place values for the focus adjustment mechanism, e.g. for the scanner 8.

Turning the laser on and off while scanning a spiral pattern can create the unique asymmetrical shapes shown in a reproducible way.

Figure 4:
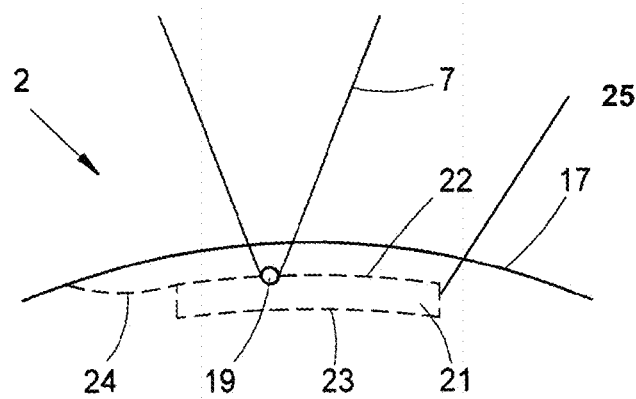
FIG. 4 shows a schematic sectional view through the cornea in order to illustrate the removal of the cornea volume in conjunction with the refractive correction by means of eye surgery according to an embodiment of the invention.

The creation of the incision surface by the treatment device 1 is shown in FIG. 4 by way of an example. A cornea volume 21 in the cornea 17 is isolated by adjusting the focus 19 in which the focused beam 7 is bundled. For this purpose, incision surfaces are created that are configured here by way of an example as an anterior flap incision surface 22 and as a posterior lenticule incision surface 23. These terms are to be understood merely by way of examples and serve to establish the link to the conventional Lasik or Flex method for which the treatment device 1, as already explained, is likewise configured. Here, the only essential aspect is that the incision surfaces 22 and 23 as well as the encircling edge incision 25 that brings the incision surfaces 22 and 23 together at their edges have to be capable of isolating the cornea volume 21. Moreover, through an opening incision 24, a cornea flap that delimits the cornea volume 21 on the anterior side can be folded back so that the cornea volume 21 can be removed.

As an alternative and in a way that is essential for the present invention, it is possible to employ the SMILE method, whereby the cornea volume 21 is removed through a small opening incision as is described in German patent application DE 10 2007 019813 A1. The disclosed content of this publication is incorporated in its entirety here.

Figure 5:
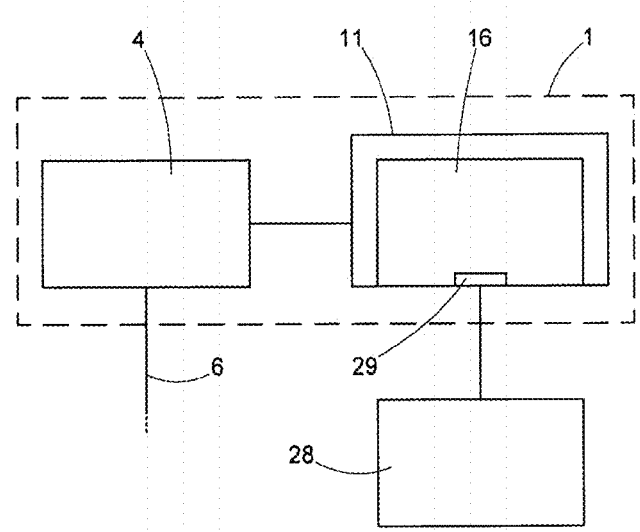
FIG. 5 shows a schematic representation of the structure of the treatment device shown in FIG. 1, with special reference to the planning system that is present therein.

FIG. 5 schematically shows the treatment device 1 and it is on this basis that the significance of the planning system 16 will be described in greater detail. In this variant, the treatment device 1 has at least two units or modules. The already described laser apparatus 4 emits the laser beam 6 onto the eye 2. The operation of the laser apparatus 4, as already described, takes place fully automatically by the control unit 11, that is to say, in response to an appropriate starting signal, the laser apparatus 4 starts to generate and deflect the laser beam 6, creating incision surfaces in this process that are structured in the manner already described. The laser apparatus 5 receives the control signals needed for the operation from the control unit 11, which has previously been provided with the applicable control data. This is done by the planning system 16, which is shown in FIG. 5 merely by way of example as a component of the control unit 11. Of course, the planning system 16 can also be configured on its own and can communicate with the control unit 11 via a hard-wired or wireless connection. The only essential aspect is that an appropriate data transmission channel has to be provided between the planning system 16 and the control unit 11.

The planning system 16 generates a control data record that is made available to the control unit 11 in order to perform the refractive correction by means of eye surgery. Here, the planning system uses measured data about the cornea of the eye. In the embodiment described here, this data comes from a measuring device 28 that has previously measured the eye 2 of the patient. Of course, the measuring device 28 can be configured and can transmit the applicable data to the interface 29 of the planning system 16 in any desired manner.

The planning system now assists the operator of the treatment device 1 in defining the incision surface for isolating the cornea volume 21. This can go as far as being a fully automatic definition of the incision surfaces, which can be carried out, for example, in that, on the basis of the measured data, the planning system 16 specifies the cornea volume 21 that is to be removed, then defines its boundary surfaces as incision surfaces, and generates appropriate control data for the control unit 11. At the other end of the degree of automation, the planning system 16 can have an input device where a user enters the incision surfaces in the form of geometric parameters, and the like. Intermediate stages involve proposals for the incision surfaces that the planning system 16 generates automatically and that can be modified by an operator. Fundamentally, all of the concepts that were already explained above in the more general description part can be used in the planning system 16.

In order to carry out a treatment, the planning system 16 generates control data for creating the incision surface, and this data is then used in the treatment device 1.

FIG. 6a shows a schematic representation of a cornea cross section according to the state of the art using a SMILE method for illustrating the geometric situation. The cornea 17 has an anterior cap incision 22 with an opening incision 26. The posterior lenticule incision 23 isolates the lenticule volume 21, which can be removed through the opening incision 26.

Figure 7:
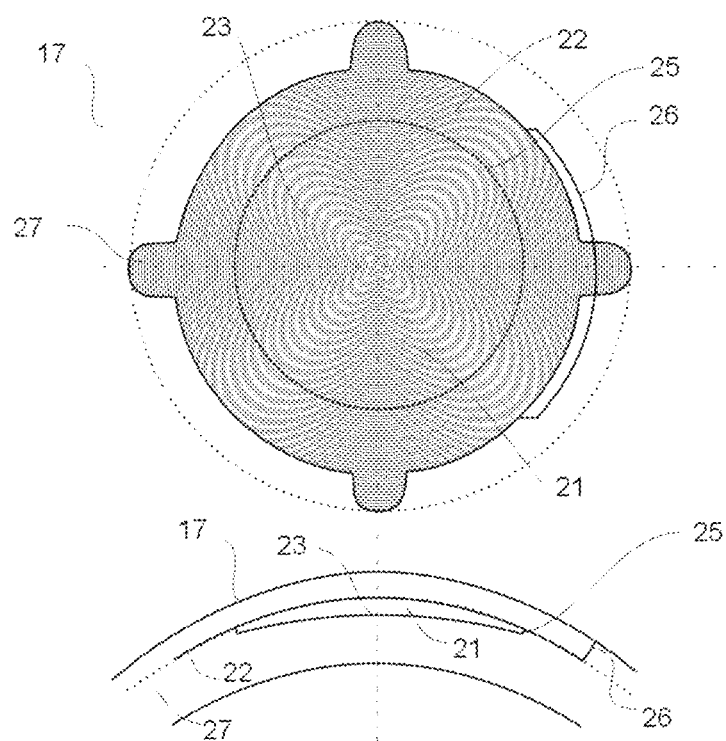
FIGS. 7 and 8 show schematic representations of SMILE cap incision geometries according to an embodiment of the invention.

FIG. 7a shows a schematic representation according to one embodiment of the invention. The cap incision 22 and the lenticule incision 23 correspond to the situation already shown in FIG. 6a. The cap incision 22, whose diameter is greater than the diameter of the lenticule incision 23, has extensions 27 directed outward to the surrounding corneal tissue. These extensions 27 are in the same depth from the surface of the cornea 17 as the cap incision 22, approximately 100 to 180 μm.

FIG. 7b shows a top view of the cornea depicted in FIG. 7a. The width of the extensions 27 is about 10 to 100 μm but can be also up to 750 μm. In this example the number of the extensions 27 is four but can be also greater.

Figure 8:
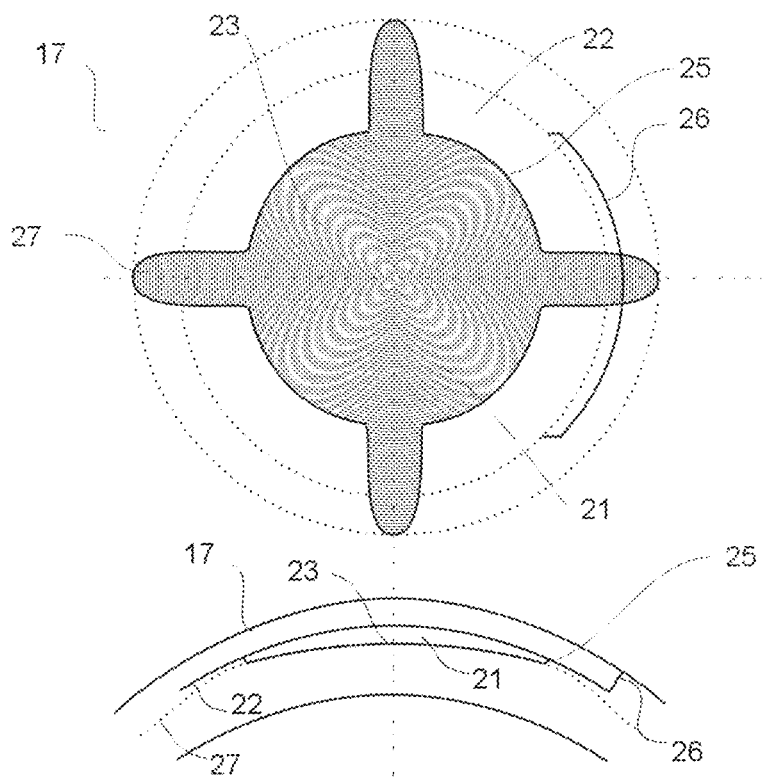

FIG. 8a shows a schematic representation according to another embodiment of the invention. The cap incision 22 and the lenticule incision 23 correspond to the situation already shown in FIG. 6a. The lenticule incision 23, whose diameter is approximately 0.1 to 1.0 mm smaller than the diameter of the cap incision 22, has extensions 27 directed outward to the surrounding corneal tissue. Here the depth of the extension 27 is increasing starting at the depth of the lenticule incision 23 to approximately 150 to 250 μm.

FIG. 8b shows a top view of the cornea depicted in FIG. 7a. The width of the extension 27 is about 50 to 200 μm but can be also up to 1000 μm. Also in this example the number of the extensions 27 is four but can be also greater.

These extensions 27 can be cut by directing the laser spot on a circular path and switching the laser on and off on the determined coordinates. They can also be cut by directing the laser spots to the desired positions inside the extensions 27 only.

The irregular shape of the extensions can alternatively be produced by directing the focused laser beam 7 also to points outside the optical defined zone of the contact glass 45. In such a case the outer shape of the cut will not be defined by the control unit 11 but by the border of the optical zone of the contact glass 45 which may be not exactly defined.

The irregular shaped portion of the laser beam cuts are peripheral to the optically important portion of the cornea and are not expected to effect the refractive result of the treatment.

It should be additionally pointed out that, of course, the treatment device 1 or the planning system 16 are also capable of concretely implementing the method described in general terms above.

Another embodiment of the planning system is in the form of a computer program or of an appropriate data medium with a computer program that implements the planning system on an appropriate computer, so that the measured data is input via suitable data transmitters to the computer and the control data is transmitted from this computer to the control unit 11, for which purpose, once again, data transmitters known to the person skilled in the art are employed here.

The implementation of an asymmetric pattern of femtosecond laser pulses in corneal tissue where the initial cutting is performed in a spatially unique manner resulting in improved distribution of plasma bubbles such that both improve, tissue cutting efficiency and/or reduced distortion of the tissue being cut. This new cutting pattern has the benefit of allowing a precise production of the intended computer programmed shape intended for the correction of refractive error (FLEx or SMILE) or the separation of a flap in the performance of LASIK.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B." Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise.

What is claimed is:

1. A method for eye surgery in which a treatment device creates incision surfaces in a cornea using a laser apparatus, the method comprising:
   providing cornea data based on data of a refractive correction;
   specifying the cornea incision surfaces on the basis of the cornea data and generating a control data record for the cornea incision surfaces, the cornea incision surfaces including:
      a cap incision surface disposed beneath a surface layer of corneal tissue and partially defining a lenticule volume to be removed, the cap incision surface being irregularly shaped and having extensions into surrounding tissue,
      a lenticule incision surface disposed beneath the cap incision surface, the lenticule incision surface having a smaller diameter than the cap incision surface,
      an edge incision that brings the lenticule incision surface and the cap incision surface together so as to isolate the lenticule volume to be removed, and
      an opening incision configured to enable the lenticule volume to be removed from the cornea;
   transmitting the control data to the treatment device; and
   creating the cornea incision surfaces by controlling the laser apparatus based on the control data record.

2. The method recited in claim 1, wherein the lenticule incision surface has a smaller diameter than the cap incision surface.

3. The method as recited in claim 2, wherein the diameter of the lenticule incision surface is 0.1 to 1.0 mm smaller than the diameter of the cap incision surface.

4. The method as recited in claim 1, wherein a width of the extensions into the surrounding tissue have a width of from 10 µm to 750 µm.

5. The method as recited in claim 1, wherein a depth, from a surface of the cornea, of the extensions into the surrounding tissue is from 100 µm to 180 µm.

6. The method as recited in claim 1, wherein the lenticule incision surface partially defines the lenticule volume to be removed, is irregularly shaped, and has second extensions into surrounding tissue.

7. The method as recited in claim 6, wherein all of the second extensions into the surrounding tissue of the cap incision surface are arranged symmetrically around a periphery of the lenticule incision surface.

8. The method as recited in claim 6, wherein a width of the second extensions into the surrounding tissue is of from 50 µm to 1000 µm.

9. The method as recited in claim 6, wherein a depth, from a surface of the cornea, of the second extensions into the surrounding tissue is from 150 µm to 250 µm.

10. The method as recited in claim 6, wherein the cap incision surface is located at a first depth beneath an exterior surface of the cornea, wherein the lenticule incision surface is located at a second depth beneath the exterior surface of the cornea, wherein the extensions into the surrounding tissue of the cap incision surface are located at the first depth beneath the exterior surface of the cornea, and wherein the second extensions into the surrounding tissue of the lenticule incision surface are located at the second depth beneath the exterior surface of the cornea.

11. The method as recited in claim 6, wherein the second extensions into the surrounding tissue of the lenticule incision surface have a depth that increases from a base of the second extensions to an outermost end of the second extensions.

12. The method as recited in claim 1, wherein all of the extensions into the surrounding tissue of the cap incision surface are arranged symmetrically around a periphery of the lenticule incision surface.

13. The method as recited in claim 1, wherein the extensions into the surrounding tissue of the cap incision surface are located beneath the surface layer of the corneal tissue such that the extensions into the surrounding tissue of the cap incision surface are not present at an exterior surface of the cornea.

14. The method as recited in claim 1, wherein the access incision is disposed, in a depth direction, above the cap incision surface and is further disposed, in a radial direction, between a first diameter of the cap incision surface defined by a base of the extensions into the surrounding tissue and a second diameter of the cap incision surface defined by an outermost end of the extensions into the surrounding tissue.

15. A tangible non-transient computer-readable medium having computer-executable instructions stored thereon, the computer-executable instructions including instructions for:
   providing cornea data based on data of a refractive correction;
   specifying the cornea incision surfaces, the cornea incision surfaces including:
      a cap incision surface disposed beneath a surface layer of corneal tissue and partially defining a lenticule volume to be removed, the cap incision surface being irregularly shaped and having extensions into surrounding tissue,
      a lenticule incision surface disposed beneath the cap incision surface,
      an edge incision that brings the lenticule incision surface and the cap incision surface together so as to isolate the lenticule volume to be removed, and
      an access incision configured to enable the lenticule volume to be removed from the cornea; and
   generating a control data record for the cornea incision surfaces for purposes of controlling the laser apparatus.

16. The tangible non-transient computer-readable medium recited in claim 15, further comprising computer-executable instructions including instructions for:
   transmitting the control data to the treatment device; and
   creating the cornea incision surfaces by controlling the laser apparatus based on the control data record.

17. The tangible non-transient computer-readable medium recited in claim 15, wherein the lenticule incision surface has a smaller diameter than the cap incision surface.

18. The tangible non-transient computer-readable medium recited in claim 15, wherein all of the extensions into the surrounding tissue of the cap incision surface are arranged symmetrically around a periphery of the cap incision surface.

* * * * *